United States Patent [19]

Wu

[11] Patent Number: 5,670,380

[45] Date of Patent: Sep. 23, 1997

[54] ASSAY FOR FETAL THYROID FUNCTION

[76] Inventor: Sing-Yung Wu, 3114 Marna, Long Beach, Calif. 90808

[21] Appl. No.: 273,104

[22] Filed: Jul. 8, 1994

Related U.S. Application Data

[63] Continuation-in-part of Ser. No. 238,173, May 4, 1994, abandoned.

[51] Int. Cl.$^6$ .......................... G01N 33/53; G01N 33/566
[52] U.S. Cl. .......................... 436/500; 436/501; 435/7.1
[58] Field of Search .......................... 435/7.1; 436/500, 436/501

[56] References Cited

PUBLICATIONS

Bachrach, L.K., et al.; *Thyroid function in pregnancy: fetal--maternal relationships;* Pediat. Adolesc. Endocr., 14:1–18, 1985.

Chopra, I.J., et al.; *A radio-immunoassay for measurement of 3,5,3'-triiodothyronine sulfate: studies in thyroidal and nonthyroidal diseases, pregnancy, and neonatal life;* J. Clin Endocrinol Metab 75:189–194, 1992.

Eelkman–Rooda, E.J., et al.; *Development of a readioimmunoassay for triiodothyronine sulfate;* J. Immunoassay 9(2):125–134, 1988.

Fisher, D.A., et al; *Early treatment of congenital hypothroidism;* Pediatrics 83:785–789, 1989.

McKenzie, J.M., et al.; *Fetal and neonatal hyperthyroidism and hypothyroidism due to maternal TSH receptor antibodies;* Thyroid 2:155–159, 1992.

Mol, J.A., et al.; *Synthesis and some properties of sulfate esters and sulfamates of iodothyronines;* Endocrinology 117:1–7, 1985.

Perelman, A.H., et al.; *Interauterine diagnosis and treatment of fetal goitrous hypothyroidism;* J. Clin. Endocrinol Metab 71:618–621, 1990.

Polk, D.H., et al.; *Metabolism of sulfoconjugated thyroid hormone derivatives in developing sheep;* Am J. Physiol 266 (Endocrinol Metab 29) :E892–E896, 1994.

Robuschi, G., et al.; *Amniotic fluid thyrotropin (TSH) following maternal administration of thyrotropin releasing hormone;* J. Perinat Med 13: 219–226, 1985.

Thorpe–Beeston, J.G., et al.; *Fetal thyroid function;* Thyroid 2:207–217, 1993.

Wu, S.Y., et al.; *Maturation of thyroid hormone metabolism, in: Thyroid hormone metabolism: regulation and clinical implications;* S.Y. Wu (ed.) Blackwell Scientific C/Publications, Inc., Cambridge Mass., 1991.

Wu, S.Y., et al.; *Identification of thyroxine–sulfate ($T_4S$) human serum and amniotic fluid by a novel $T_4S$ radioimmunoassay;* Thyroid 2:101–105, 1992.

Wu, S.Y., et al.; *The development of a radioimmunoassay for reverse triiodothyronine sulfate in hyman serum and amniotic fluid;* J. Clin Endocrinol Metab 76:1625–1630, 1993.

Wu, S.Y., et al.; *Sulfate conjugates of iodothyronines in developing sheep: effect of fetal hypothyroidism;* Am J. Physiol 265 (Endocrinol Metab 28) : E115–E120, 1993.

Wu, S.Y. et al.; *A 3,3'–diiodothyronine sulfate cross–reactive compound in serum from pregnant women;* J. Clin Endocrinol Metab 78: 1505–1509.

*Primary Examiner*—Toni R. Scheiner
*Attorney, Agent, or Firm*—Knobbe Martens Olson & Bear, LLP

[57] ABSTRACT

Disclosed is an assay for fetal thyroid function involving determining the amount of fetal thyroid function indicator that is present in the maternal blood and maternal urine and then comparing the determined value to a known standard for the gestation age of the fetus. It is defined as below one standard deviation of the normal values. Also disclosed is a method of treating a fetus having hypothyroidism involving determining that the fetus is hypothyroid using the assay of the present invention and thereafter, administering supplemental thyroid hormone ($T_4$, 500 ug/wk) into the amniotic sac. Also disclosed is a method of identifying euthyroid state using the assay of the present invention in hypothyroid fetuses receiving $T_4$ therapy.

5 Claims, 4 Drawing Sheets

ASSAY FOR FETAL THYROID FUNCTION

RELATED APPLICATIONS

This application is a continuation-in-part of application Ser. No. 08/238173, filed May 4, 1994, now abandoned.

FIELD OF THE INVENTION

The present invention relates to methods of detecting inadequate fetal thyroid function and to treating a fetus having inadequate fetal thyroid function in order to prevent or lessen the associated sequelae.

BACKGROUND OF THE INVENTION

Prenatal hypothyroidism can result in a syndrome known as cretinism. This syndrome can be manifested at birth by jaundice, umbilical hernia, noisy respirations, hypotonia, depressed reflexes and lethargy, and after birth by the development of abnormal facial features, retarded bone development, enlarged tongue and constipation.

Most significantly, inadequate thyroid function prior to birth can cause abnormal neurologic development including mental retardation, varying degrees of deafness and a combination of flexed posture with spasticity and rigidity of proximal limb musculature. These nervous system deficits can persist throughout life.

Worldwide, prenatal hypothyroidism most commonly results from a maternal iodine deficiency, particularly in some estimated 800 million people in geographic areas wherein dietary iodine deficiency is endemic. The prevalence of endemic cretinism can reach 10% of the whole population in severely affected areas. It can also result from congenital disorders of thyroid function.

Because of the potentially severe consequences, neonates are screened for hypothyroidism by measuring serum $T_4$ or TSH. However, numerous reports have shown that some infants have some degree of impaired psychological and neuromuscular function at later ages, even when therapy has been started early. Ideally, prenatal screening would allow in utero intervention to prevent or lessen the effects of prenatal hypothyroidism.

Among the thyroid hormones, concentrations of hormones resulting from the conjugation of phenolic hydroxyl with sulfate, including $T_4$ sulfate ($T_4S$), $T_3$ sulfate ($T_3S$), and $rT_3$ sulfate ($rT_3S$) are markedly elevated in fetal and newborn cord sera. The high levels of these sulfated iodothyronines in fetal serum are due to both reduced clearance secondary to relatively low type I 5'-monodeiodinase activity in fetal tissue and high fetal production rates, particularly of $T_4S$.

The high prevailing levels of sulfated iodothyronines in fetal plasma, however, are not associated with increased circulating concentrations of $T_4S$, $T_3S$, or $rT_3S$ in pregnant women. Thus, measurement of these substances in maternal serum cannot be used to detect inadequate fetal thyroid function. Similarly, analysis of amniotic fluid iodothyronine metabolites or TSH levels also cannot be used to evaluate fetal thyroid function, because the concentrations of $T_4$ or $rT_3$ correlate poorly with maternal or fetal thyroid function. Whether amniotic fluid TSH reflects fetal or maternal TSH concentrations remains to be established.

Currently, direct sampling of fetal blood levels of fetal thyroid hormone or metabolites of fetal thyroid hormone requires an invasive procedure in the uterus. This procedure of cordocentesis is expensive, requires highly trained personnel and carries a significant risk of injury to the fetus.

Thus, there remains a need for an effective prenatal test to determine fetal thyroid function. In one aspect, the present invention is an improved method of testing for prenatal hypothyroidism by screening the mother's blood for a novel compound.

SUMMARY OF THE INVENTION

In one aspect, the present invention is an assay for quantifying fetal thyroid function of a fetus in a pregnant woman. The assay comprises the steps of, first, obtaining a sample of fluid from the pregnant woman, wherein the fetus has a gestational age; next, determining the amount of Fetal Thyroid Hormone Indicator (FTFI) present in the fluid, wherein the FTFI has the characteristics of immunological cross-reactivity with L-3,3'-diiodothyronine ($T_2$) sulfate ($T_2S$), presence in cord blood at birth, crosses the placenta, presence in maternal blood in a concentration versus weeks of gestation having a relative relationship as shown by a best fit expressed as $y=57-2.9x+0.17x^2$, wherein y is expressed as nanomoles/L or ng/dL $T_2S$ equivalent and x is weeks of gestation, and has a different chromatographic peak than synthetic $T_2S$ in high pressure liquid chromatography; and then, comparing the amount of determined FTFI to a known normal amount of FTFI for the gestational age. A determined FTFI amount lower than about one standard deviation of the normal FTFI amount for the gestation age indicates abnormally low thyroid function in the fetus.

In one embodiment the assay is performed using maternal blood. In another, the assay is performed using maternal urine.

In another aspect of the present invention, there is provided a method of treating a fetus having inadequate thyroid function, comprising the steps of, first, identifying the fetus as having inadequate thyroid function according to the assay for quantifying fetal thyroid function of a fetus in a pregnant woman of the present invention, and then treating the fetus to render the fetus closer to a euthyroid state.

In one embodiment, the treating step comprises administering thyroid hormone to the fetus is an amount and frequency sufficient to render the fetus closer to the euthyroid state. In one particular embodiment, the thyroid hormone is $T_4$.

In another embodiment, the treating step comprises administering thyroid hormone to the fetus through the amniotic sac in a dose between about 200–800 μg weekly.

In another, the present invention is a substance present in fetal blood, comprising a compound that has the following characteristics: 1) immunological cross-reactivity with $T_2$ sulfate ($T_2S$), 2) presence in cord blood at birth, 3) capability of crossing the placenta, 4) presence in maternal blood in a concentration versus weeks of gestation having relative relationship as shown by a best fit expressed as $y=57-2.9x+0.17x^2$, wherein y is expressed as nanomoles/L or ng/dL $T_2S$ equivalent and x is weeks of gestation, 5) presence in maternal urine in increasing quantities with progression of pregnancy when expressed in ng/gram of urinary creatinine, and 6) a different chromatographic peak than synthetic $T_2S$ in high pressure liquid chromatography.

DETAILED DESCRIPTION OF THE PREFERRED EMBODIMENTS

Figure 1:
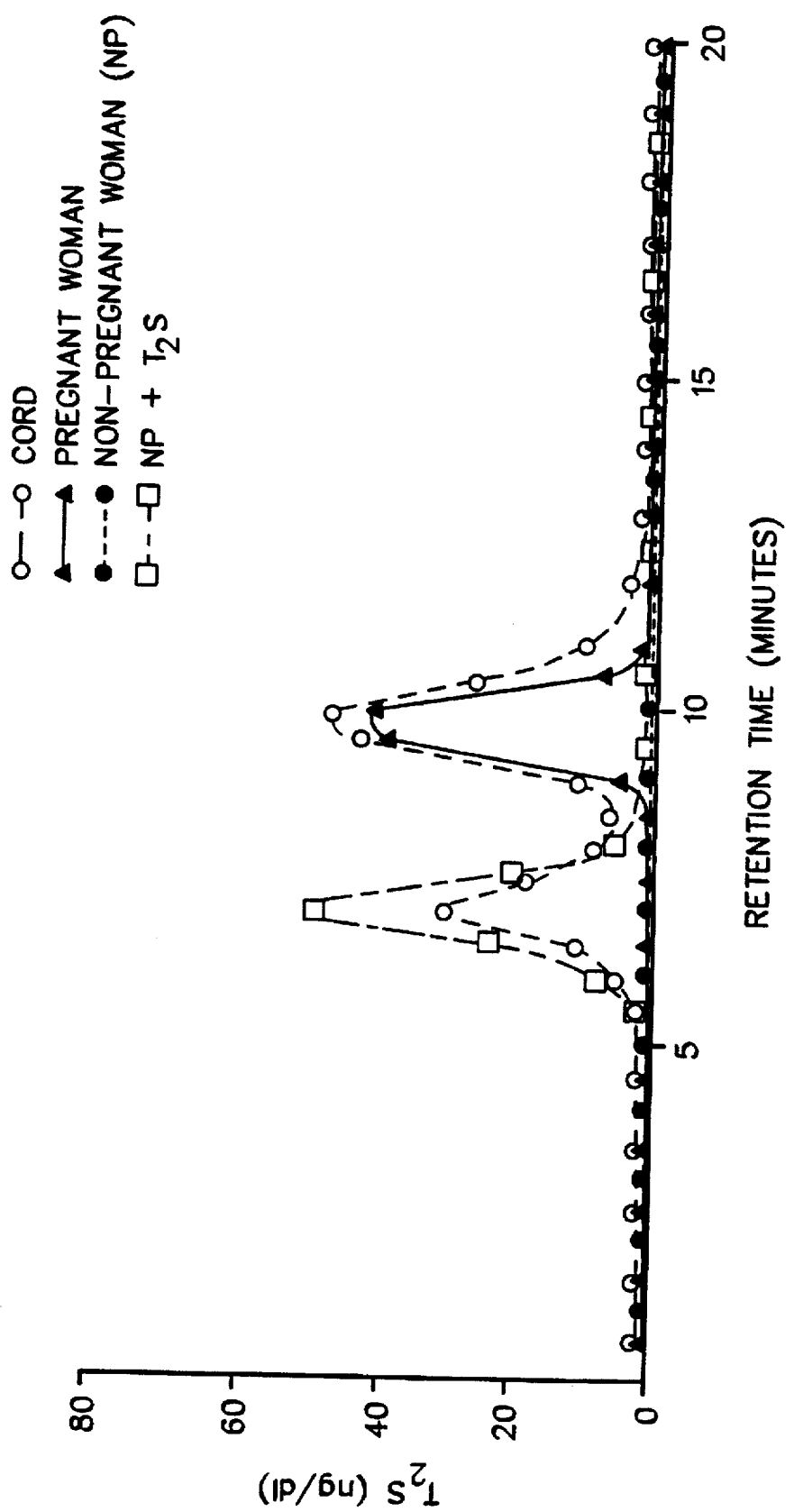
FIG. 1 is a plot of $T_2S$ and FTFI concentration identified by the invented sensitive RIA in serum extract from pregnant women, non-pregnant women with and without supplementation of $T_2S$, and cord blood fractionated on HPLC.

It is one goal of the present invention to provide an improved method of testing for prenatal hypothyroidism which will allow for timely treatment of the condition to prevent or lessen the associated sequelae. In one embodiment, the present invention related to the discovery of a substance hereinafter referred to as "Fetal Thyroid Function Indicator" (FTFI). This substance is present in human maternal serum and urine in concentrations that increase progressively to peak values before parturition. After parturition, FTFI is cleared from the maternal circulation in 7–10 days.

FTFI was discovered unexpectedly during experiments to determine whether 3,3'-diiodothyronine sulfate ($T_2S$) levels were elevated in pregnant women. Serum $T_2S$ immunoreactivity was measured in non-pregnant women and in pregnant women at various gestational ages as well as after delivery using the method described below. It is one of the surprising discoveries of the present invention that maternal levels of FTFI can be used to identify deficient thyroid function in the fetus.

METHODS AND MATERIALS $T_2S$ Radioimmunoassay 3,3'-$T_2S$ and [$^{125}$I]$T_2S$ were prepared by the method of Eelkman-Rooda and co-workers (Eelkman-Rooda SJ, Kaptein E, VanLoon MAC, Visser TJ. 1988 "Development of a radioimmunoassay for triiodothyronine sulfate"), herein incorporated by reference in its entirety, but can be prepared by any number of methods known to those with skill in the art. L-3,3'-Diiodothyronine (L-$T_2$) is purchased from Henning Berlin (Berlin, Germany). The radioactive [$^{125}$I] $T_2$ (S.A. 300–500 mCi/mg) was prepared by iodination of 3,3'-$T_2$ (exchange reaction) using methods described in Nakamura Y, Chopra IJ, Solomon DH. 1977 "Preparation of high specific activity radioactive iodothyronines and their analogues." *Journal of Nuclear Medicine.* 18:1112–1115, herein incorporated by reference in its entirety, but can be prepared by any of a number of methods known to those with skill in the art. In 10×75 mm disposable glass culture tubes, 10 μl of methanol containing $10^{-9}$ moles of the substrate ($T_2$) were mixed with 25 μl of 0.4 M phosphate buffer (pH 6.2) containing approximately 1 mCi of I-125. The radioiodination reaction was started by adding 10 μl of 0.05M phosphate buffer (pH 6.2) containing 4 μg of chloramine-T. Two minutes later, the reaction was stopped by addition of 20 μl of a solution prepared by 1:10 dilution of saturated sodium metabisulfite in 0.05 M phosphate buffer (pH 6.2). The reaction mixture was next transferred to a column made from a 3-mL disposable plastic syringe filled with a suspension of Sephadex LH-20 up to 1.2 mL; the reaction vessel was washed once with 50 μl of 0.05 M phosphate buffer (pH 6.2), and washings were also transferred to the column. Unreacted radioiodine was removed by washing of the column with 1 mL of 0.05M phosphate buffer (pH 6.2) followed by 4 mL of water and 0.6 mL 99:1 (methanol: 2N $NH_4OH$). The radioactive compounds were then eluted with 4 mL of 99:1 (methanol: 2N $NH_4OH$) and were dried under a thin stream of air. The residue was dissolved in 100 μl of methanol (2N $NH_4OH$) and applied to a paper strip to separate the radioiodinated iodothyronines.

Descending paper chromatography was performed using a 1:5:6 hexane: tertiary amyl alcohol: 2N $NH_4OH$ system and 3 MM Whatman chromatographic paper. Chromatography was allowed to proceed for 20 hr. The radioactive spots were identified by a X-ray film overlaying the paper chromatographic strip for 1 min. The radioactive spots were cut and eluted with 5–10 mL of 99:1 methanol-2N $NH_4OH$. The eluate was dried under air and the residue dissolved in 1–3 mL of 50% propylene glycol for storage at 4° C. The [$^{125}$I]-$T_2$ spot was identified by specific $T_2$ antibody by RIA.

Radioactive tracer amounts of 125-I-$T_2S$ or relatively small quantities (ng to μg) of $T_2S$ were synthesized as following. Reactions involving cholorosulfonic acid were started by the slow addition of 200 μl chlorosulfonic acid ($ClSO_3H$, 15 M, Aldrich Chemical Co., Milwaukee, Wis.) to 800 μl N,N-dimethylformamide (DMF) at 0° C. In another tube, a solution of (usually) 100 pmol unlabeled plus [$^{125}$I]-$T_2$ in ammonia ethanol was evaporated under a stream of nitrogen. To the residue of the latter tube, 200 μl of the $ClSO_3H$ solution in DMF was added at 0° C. Subsequently, the mixtures were brought to room temperature, and, in general, reactions were continued overnight. After dilution with 800 μl ice-cold water, reaction products were analyzed by Sephadex LH-20 chromatography. Products were applied to a small 1-mL Sephadex LH-20 column. Serial elution was performed with 4×1-mL fractions of 0.1N HCl, 7×1-mL water, and 4×1-mL of 1N ammonia in ethanol. The sulfated $T_2$ was eluted with water.

Larger (mg) quantities of $T_2S$ were similarly synthesized. Five to 20 mg anhydrous $T_2$ (Sigma) and 1 μCi $^{125}$I-$T_2$ was added to 0.5 mL of a mixture of $ClSO_3H$ and DMF (¼, v/v) at 0° C. After reacting for 40 hours at room temperature, $T_2S$ was precipitated by addition of this mixture to 5 mL $H_2O$ at 0° C. The pellet was dissolved in 1 mL 2N $NH_4OH$ and reprecipitated with 5 mL1 N HCl. The pellet was further washed by repeated suspension in 3 mL 0.1 N HCl.

Identification and further purification of $T_2S$ had been achieved by HPLC. Reverse phase HPLC was performed on a Radial PAK uBondapak $C_{18}$ column using a model 6000A solvent delivery system, and absorbance was monitored at 254 nm with a variable wavelength detector (Waters, Milford, Mass.). Products were eluted isocratically with a mixture of acetonitrile and 0.02M ammonium acetate, pH 4 (22:78, v/v), at a solvent flow of 2 mL/min. Absorbance was recorded at 254 nm. A semipreparative column (Blochtom 1010 ODS, Regis) was used for separation and quantitative recovery of other pure iodothyronine sulfate conjugates including $T_2S$.

The $T_2S$ (approx. 1–5 mg, with tracer amount of 125-I-$T_2S$) was dissolved in 5 mL dimethylformamide and added to a solution of 100 mg bovine albumin (BSA) in 20 mL $H_2O$. After adjusting the mixture to pH 5 with 0.1 N NaOH, 50 mg 1-ethyl-3-(3-dimethylaminopropyl) carbodiimide (Sigma Co., St. Louis, Mo.) was added in 5 mL $H_2O$. This was repeated after 3 hr, and the mixture was further stirred for 16 hr at room temperature. The product was dialyzed at 4° C. against successively 2×2 liter $H_2O$, 2 liter 0.1N NaOH and 3×2 liter $H_2O$, changed twice daily. Analysis of the remaining radioactivity indicated a low degree of $T_2S$ incorporation (<5%), corresponding to <5 mol $T_2S$/mol BSA. The immunogen was stored at −20° C. in a concentration of 1.5 mg protein/mL. Three New Zealand white rabbits were immunized by S.C. injections of 1 mL conjugates mixed with complete Freund's adjuvant at multiple sites in the back. This was repeated after one month and subsequently at bimonthly intervals.

The RIA employed an anti-L-$T_2S$ (WO213) obtained from rabbits immunized with L-$T_2S$ BSA conjugate. In a final dilution of 1:15,000, anti-$T_2S$ antibody WO213 bound 35–45% of a tracer amount (~5 pg or 6.8 fmol) of [$^{125}$I]$T_2S$ in 0.075 mol/L barbitol buffer (pH 8.6; containing 0.15% sodium azide and 0.125% normal rabbit serum) and 19% ethanol.

The $T_2S$ RIA procedure was performed using serum or urine samples that were extracted with 2 volumes 95% ethanol (final concentration, 63%) before assay. Preliminary experiments showed that the extraction efficiency of $T_2S$ in serum exceeded 96%. Final $T_2S$ concentrations were not corrected for recovery. The lower limit of detection of the assay was 8.3 fmol (5 pg) or 82.6 pmol/L in a 300-μl ethanol extract of serum.

The cross-reactivities of various thyroid hormone analogs were determined using this assay. Only $T_4S$, $rT_3S$ and $T_3S$ cross-reacted significantly (3.2%, 1.4%, and 0.02%, respectively). Other thyroid hormone analogs and sulfated steroids (dehydroepiandrosterone sulfate, estradiol sulfate and estrone sulfate) cross-reacted less than 0.0001%.

Identification of FTFI

FTFI was identified during determination of $T_2S$ in the following manner. $T_2S$ immunoreactivity was determined in maternal serum or urine extracts by acid hydrolysis, HPLC, and RIA. Ten to 20 mL maternal serum or urine were extracted with 2 volumes 95% ethanol and subsequently lyophilized. The dried extracts were dissolved in 1–2 mL $H_2O$ and purified with an LH-20 column. One milliliter of the solubilized extract was applied to a small LH-20 column (bed volume, 1.2 mL) equilibrated in 0.1 mol/L HCl.

Next, the column was rinsed with 4 mL 0.1 mol/L HCl. The ensuing 7 mL $H_2O$ eluent fractions were collected and lyophilized. The dried fractions were dissolved in 500 μl 0.025 N NaOH.

After application of 200 μl sample to a HPLC uBondapak $C_{18}$ column, the serum extract was eluted isocratically with a mixture of acetonitriles and 0.02 mol/L ammonium acetate, pH 4.0 (22:78, vol/vol) at a flow rate of 2 mL/minutes. Aliquots of eluent of 1-mL fractions were collected, and 100 μl of these aliquots were subjected to $T_2S$ RIA. Radioactive or non-radioactive $T_2S$-supplemented serum extracts from non-pregnant women were used to identify the $T_2S$ peak.

One milliliter of 63% ethanol serum extract was mixed with 1 mL 1.0N HCl, followed by heating at 80° C. for 1 hour to hydrolyze sulfated iodothyronines. After the addition of 1 mL 1N NaOH, the concentration of 3,3'-$T_2$ was measured in duplicate 300-μl aliquots of the resulting mixture by specific RIA.

Sources of Specimens

Serum samples were obtained from 200 pregnant women with estimated gestational ages ranging from 3–40 weeks (18–39 years of age). Serum samples were also obtained from 25 women (20–39 years of age) at the time of delivery and from paired newborn cord blood samples. Additionally, 67 serum samples were obtained from 35 women 12–184 hours postpartum. Control samples were obtained from 14 normal non-pregnant women, 19–35 years of age (NP control). Urine samples were also obtained from 85 pregnant women with estimated gestational ages ranging from 4–40 weeks.

Statistical Analysis

Student's unpaired t test was used to assess between-group differences. Analysis of variance was used to test multigroup comparisons. If significant differences were present, Dunnett's multicomparison test was used to compare the control or baseline mean and the mean values of other groups.

Significance was defined as P<0.05. Results are reported as the mean±SEM. In addition, simple linear and multiple regression analyses of the serum FTFI concentrations of pregnant women of different gestational ages were also performed.

RESULTS:

Identification of FTFI in Serum of Pregnant Women

Referring now to FIG. 1, there is presented the identification of $T_2S$ and FTFI by RIA in third trimester women (filled triangles) and newborn cord serum extracts (open circles) on HPLC. Serum extracts from non-pregnant women with (open squares) [or without (filled circles)] supplementation of $T_2S$ were used to identify $T_2S$ peaks.

Serum extracts were eluted from HPLC (uBondapak $C_{18}$ column) isocratically with a mixture of acetonitrile and 0.02 mol/L ammonium acetate, pH 4.0 (22:78, vol/vol), at a flow rate of 2 mL/minutes. Aliquots of eluents in 1-mL fractions were collected, and 100 μL of each were studied in the $T_2S$ RIA.

Note that, in cord serum, part of the $T_2S$ immunoreactivity cochromatographed with synthetic $T_2S$ (with a retention time of 7.5 minutes), but there was an additional peak at 10 minutes. This additional peak represents FTFI in the maternal serum and urine sample.

In the serum of pregnant women, all of the $T_2S$ immunoreactivity was found in the FTFI peak. Neither $T_2S$ nor FTFI activity was identifiable in the serum of non-pregnant women.

Upon acid hydrolysis, 36±2.6% of the $T_2S$ immunoreactivity in cord serum extracts was recovered as 3,3'-$T_2$. 3,3'-$T_2$ was undetectable (<10 ng/dL) in the acid hydrolysates of serum from pregnant women. The recovery of FTFI after hot acid hydrolysis of pregnant women serum extract was 98.2±4.8% (n=10).

FTFI Concentrations in Human Maternal and Fetal Sera

A total of 200 maternal serum samples were assayed for FTFI levels. The results are shown below in Table 1. Concentrations are given in ng/dL ($T_{2S}$-equivalent)±SD(100 ng/dL=1.65 nmol/L).

Following delivery (158±11, N=25) serum levels decreased to 89±7 (N=15) at 1 day, 54±4 (N=15) at 3 days, and 20±2 (N=8) at 7 days. The peak levels remain significantly lower than the 3,3'-diiodothyronine sulfate ($T_2S$) concentrations in cord serum at birth.

TABLE 1

| | Weeks of Pregnancy | | | | | | | |
|---|---|---|---|---|---|---|---|---|
| Pt. | 3–7 | 8–13 | 14–19 | 20–26 | 27–33 | 34–40 | NB (cord) | NP |
| (N) | (38) | (33) | (38) | (18) | (51) | (22) | (45) | (15) |
| Serum Conc. (ng/dL) | 55# ±25 | 51 ±23 | 70 ±35 | 98 ±47 | 145* ±50 | 217* ±108 | 310* ±94 | 11* ±4 | in mean ± SD $T_2S$-equivalent ng/dL;
*p < 0.05 cf., 3–7 wk pregnancy;
NP = non-pregnant women,
NB = new born infant Referring now to FIG. 2, 119 pregnant women were studied at gestational ages ranging from 3–40 weeks. Serum FTFI concentrations (expressed both as nanogram/dL and as nanomoles/L $T_2S$ equivalent; mean±SE) were elevated in the first trimester (3–13 weeks pregnancy, n=41) and found to be 0.73±0.04 nmol/L (p<0.05).

The mean FTFI level increased moderately during the second trimester (14–26 weeks pregnancy, 1.14±0.09 nmol/L; n=43; p<0.05 vs. first trimester) and the first two-thirds of the third trimester (27–35 weeks, 1.67±0.11 nmol/L; n=21; p<0.01 cf. first trimester). A rather sharp increase was noted near term (36–40 weeks, 3.49±0.49 nmol/L; n=14; p<0.01 vs. first trimester).

Figure 2:
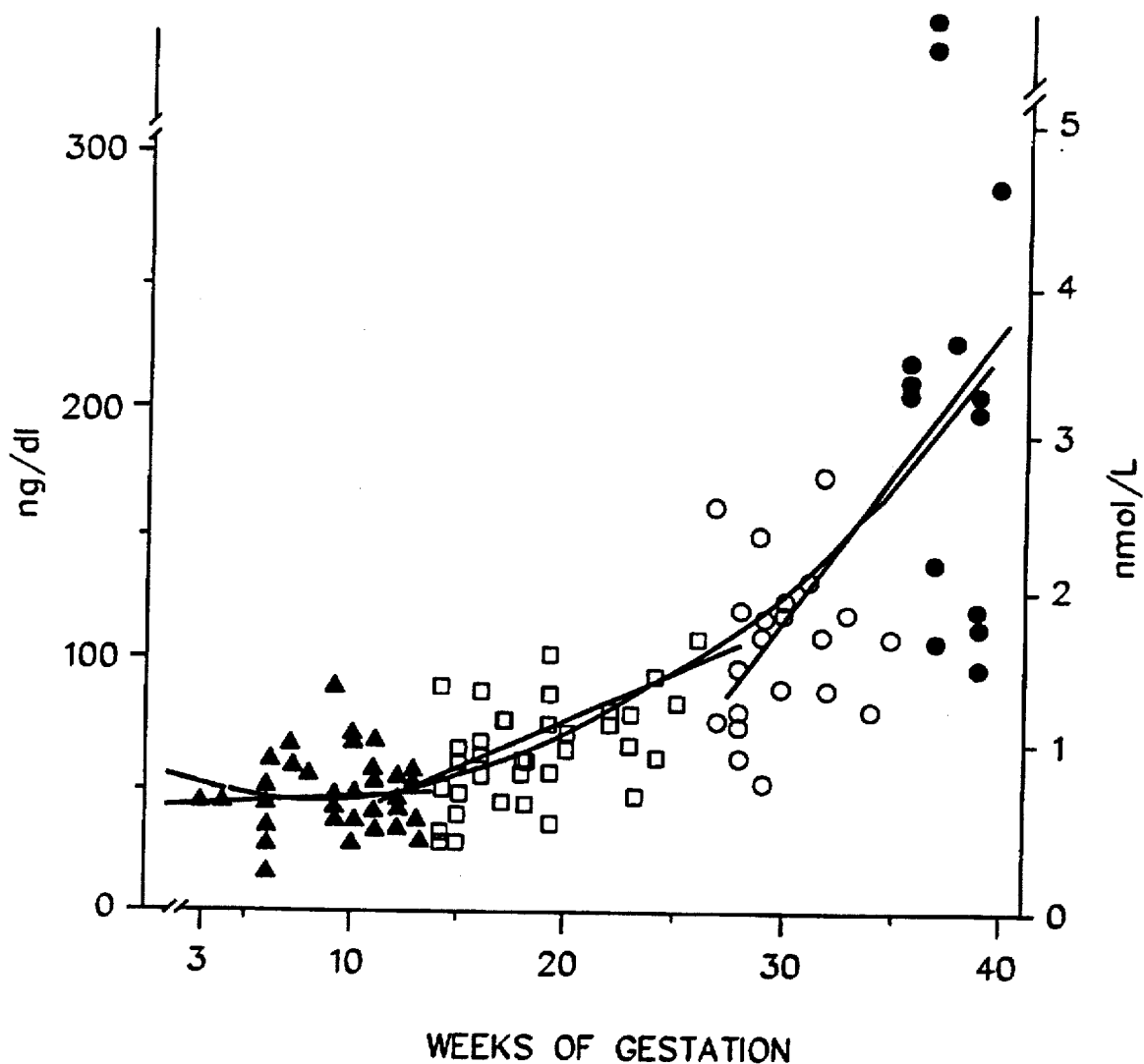
FIG. 2 is a plot of the concentration of FTFI in serum from pregnant women during various periods of gestation.

In FIG. 2, the filled triangles indicate concentrations obtained from maternal serum samples during first trimester pregnancies (3–13 weeks gestation; n=41). The open squares indicate concentrations obtained during second trimester pregnancies (14–26 weeks gestation; n=43). The circles indicate concentrations obtained during third trimester pregnancies (27–40 weeks gestation; n=35). Finally, the filled circles indicate concentrations obtained from fourteen patients approximately 1 month before delivery at term.

The straight fines labeled "A", "B", and "C" represent linear regression lines for $T_2S$ concentrations in samples from the first, second, and third trimesters (y=ax+b linear representation). The slopes of these lines were 3.69 and 10.76 for the second and third trimesters, respectively (p<0.05). Overall FTFI values in all 118 samples were best fitted by a curvilinear line (y=57−2.9×0.17$x^2$, correlation =0.7036; p<0.001).

Figure 3A:
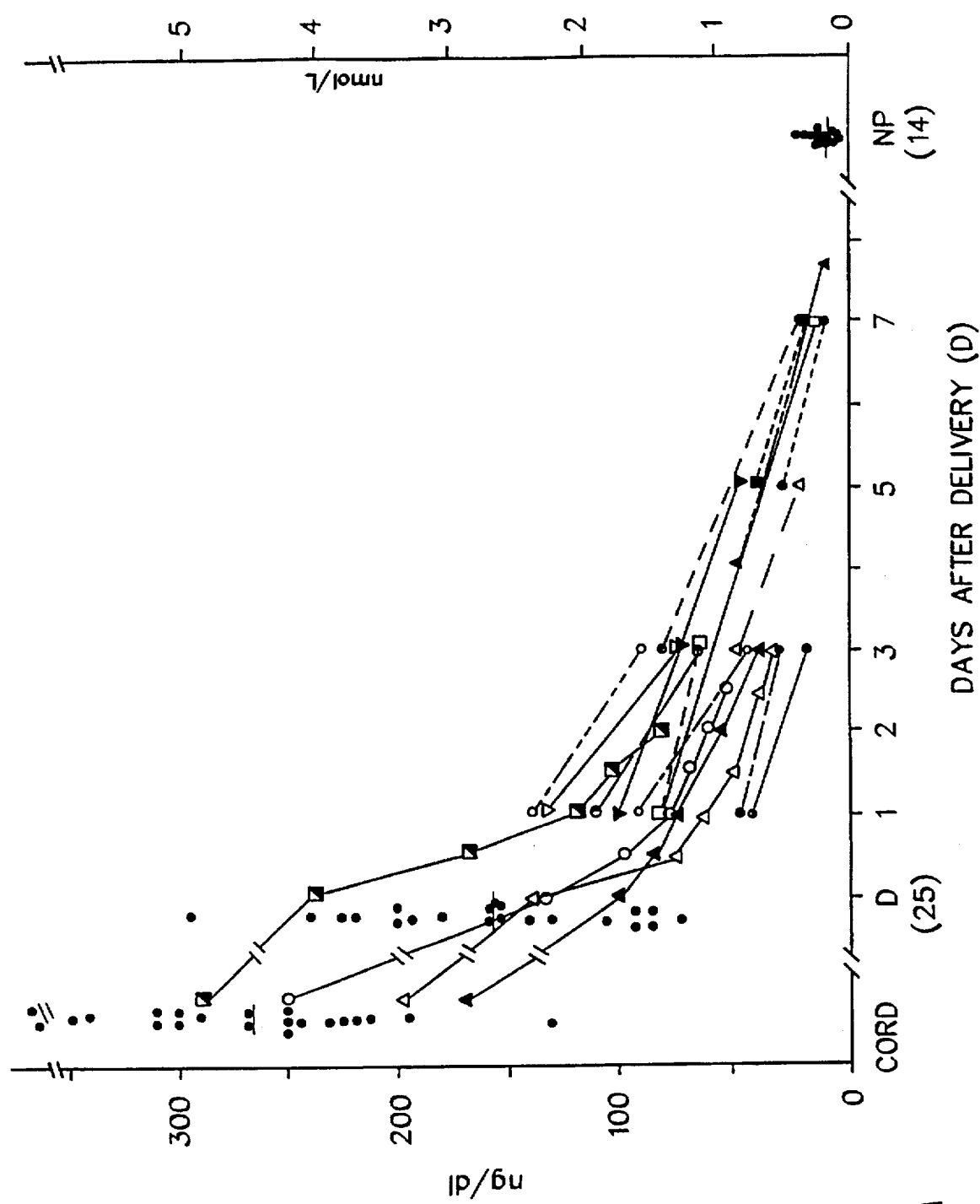
FIG. 3 is a plot of the concentration of FTFI in serum from women during the postpartum period.
Figure 3B:
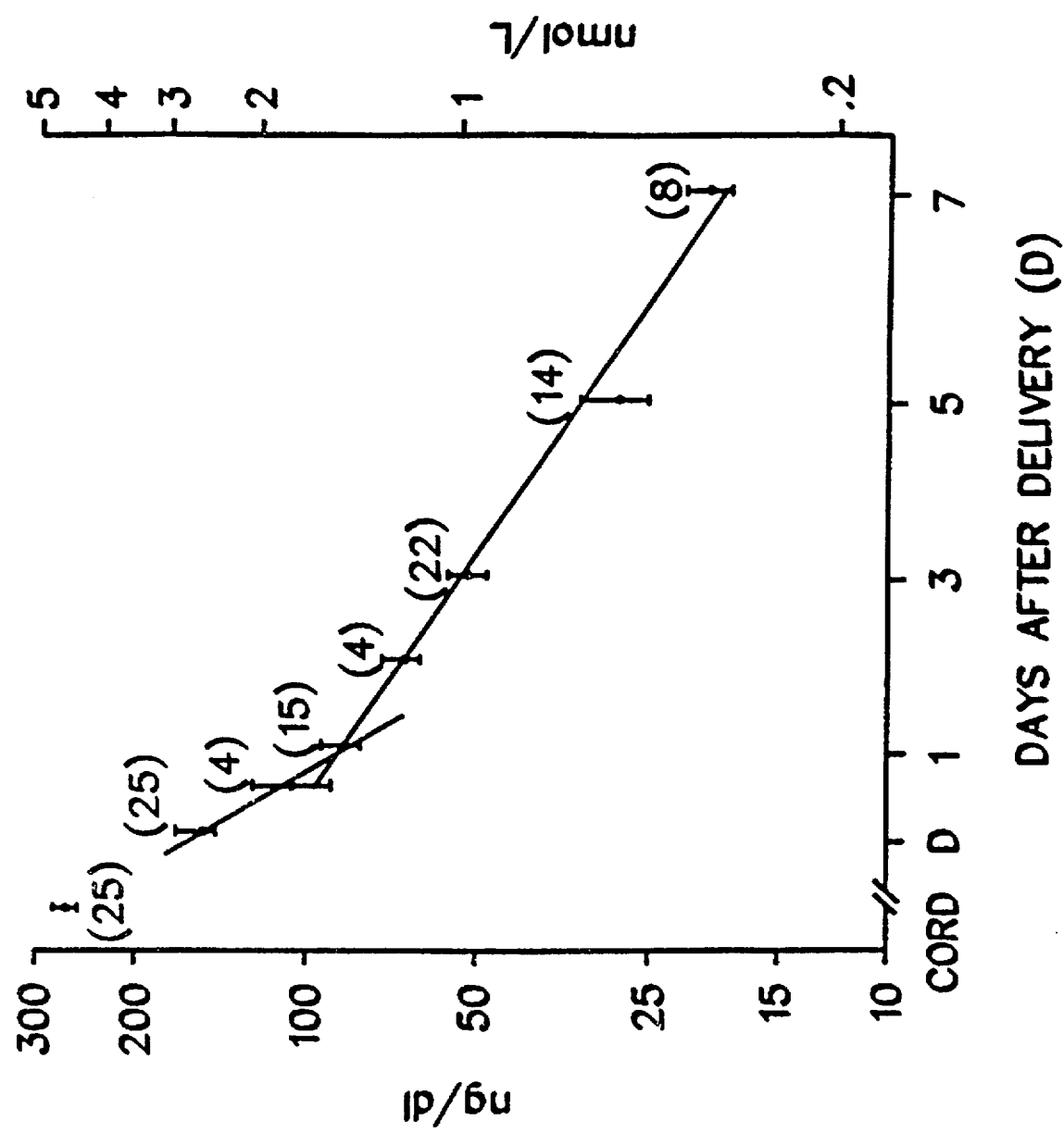

Referring now to FIG. 3, there is presented the concentrations of $T_2S$ and FTFI in cord serum of newborns and FTFI levels in maternal serum samples at the time of delivery (D). The connected lines represent serial measurements in the same patients (n=18). $T_2S$ concentrations also were measured in 14 nonpregnant women (NP) for comparison.

The decrease in serum FTFI concentrations after parturition is depicted in the semilog plot in the inset. The closed circles in vertical bars represent the mean (±SEM) and (n) represents total number of samples studied at each time period in a total of 35 patients.

As can be seen in FIG. 3, the serum levels of FTFI in pregnant women are shown at parturition (2.61±0.18 nmol/L; n=25). Immunoreactivities were measured in the paired cord sera obtained at birth (4.40±0.21 nmol/L; $T_2S$ and FTFI mixture; n=25). After parturition, maternal serum FTFI levels decreased from 2.61±0.18 nmol/L (n=25) to 1.47±0.12 nmol/L (n=18) at 1 day (decay $t_{1/2}$ =1.2 days) and then to 0.89±0.07 nmol/L (n=15) at 3 days and 0.33+0.03 nmol/L (n=8) at 7 days (decay $t_{1/2}$=2.9 days; FIG. 3).

A 6.2-fold increase in the concentration of serum $T_2S$-cross-reactive material was observed in six non-pregnant women who received hCG treatment (9 days post-hCG, 1.12±0.18 nmol/L; pre-hCG baseline concentration, 0.18±0.02 nmol/L; p<0.01). The $T_2S$-cross-reactivities remained unchanged after hot acid hydrolysis of post-hCG serum extracts.

Relation of Fetal Thyroid Function Indicator to Fetal Thyroid Hormone

The preterm increase in fetal serum FTFI appears to coincide with the known prenatal surge of serum $T_3$ in fetuses. The simultaneous peaking of fetal serum $T_3$ and maternal serum FTFI levels makes fetal serum $T_3$ a candidate for a precursor for the perinatal increases in maternal $T_2S$ levels.

In pregnant sheep near term, significant quantities of authentic [$^{125}$I]-$T_2S$ are present in the maternal compartment after the infusion of ovine fetuses with [$^{125}$I]-$T_3$. More recently it was found that fetal $T_3$ infusion rapidly increased $T_2S$ concentrations in maternal urine and serum in sheep. These results are consistent with the view that at least part of the circulating FTFI, a $T_2S$-like compound, may be fetal in origin.

An increase in FTFI levels, similar to that found in pregnant women, was found in serum of non-pregnant women who received acute injections of hCG. Thus, placental hCG may be involved in a mechanism to increase FTFI in early pregnancy. Note, however, that serum hCG concentrations peak during the first trimester and decrease progressively thereafter. Therefore, hCG cannot fully account for the continuing increase in FTFI concentrations in maternal serum during the second and third trimesters. Rather, the third trimester increase in maternal $T_2S$ immunoreactivity may be associated with the onset and progressive maturation of fetal thyroid function.

The marked rise of serum FTFI in near-term pregnant women occurs while hCG levels are relatively low and fetal serum $T_3$ levels are increasing. Thus, transplacental fetal to maternal transfer of $T_2S$ or metabolite may be involved.

FTFI Concentrations in Human Maternal Urine

FTFI and creatinine levels were measured in 85 maternal urine samples. The results are presented in Table 2, below.

Note that maternal urine FTFI concentration, expressed in ng ($T_2S$-equivalent)/gm creatinine, rises above baseline during the second trimester and continues to rise throughout the remainder of gestation. Therefore, maternal urine FTFI concentration can also be used to test for fetal hypothyroidism. In addition, urinary FTFI, expressed as ng/gram urinary creatinine, can be used as a complimentary test to serum FTFI values. It is possible that in certain patients' serum, FTFI values alone may be misleading as a result of more rapid or slow than normal clearance of serum FTFI (see case #2 below).

TABLE 2

| | Weeks of Pregnancy | | | | | | | |
|---|---|---|---|---|---|---|---|---|
| Pt. | 3–7 | 8–13 | 14–19 | 20–26 | 27–33 | 34–36 | 37–40 | NP |
| (N) | (19) | (9) | (9) | (8) | (11) | (11) | (18) | (6) |
| Urine | 601# | 697 | 814 | 1463* | 2189* | 2430* | 4323* | 338 |
| Conc. | ±155 | ±202 | ±231 | ±682 | ±1419 | ±979 | ±2057 | ±97 | in mean ± SD $T_2S$-equivalent ng/gm;
NP = non-pregnant;
*p < 0.05 cf., 3–7 wk pregnancy.

Thus, whereas hCG stimulation may account for some increase in maternal serum concentrations of FTFI in the first trimester, the more rapid increase in maternal serum FTFI concentrations during the late third trimester are probably related to changes that occur in fetal thyroid hormone economy. Further, placental transfer and transformation of fetal $T_3$ may be related to the rise in the level of FTFI in the serum of pregnant women.

EXAMPLE #1, DETECTION OF HYPOTHYROID FETUS AND INTRAUTERINE TREATMENT THEREOF

Case #1

A fetus was identified with a goiter on ultrasound examination. Cordocentesis was carried out to obtain fetal serum sample at 28 weeks of gestation. This serum sample showed a low free thyroxine value [0.6 ng/dL; (normal 0.8–2.8 ng/dL)] and elevated TSH [126 µU/mL (normal<20 µU/mL) ]. The FTFI concentration in maternal serum was also reduced, 93 ng/dL (normal mean ±SD is 145±50 ng/dL or 95–195 ng/dL). A diagnosis of potential fetal hypothyroidism was made.

The pregnant woman received an intraamniotic injection of thyroxine (levothyroxine sodium, USP, 500 µg) weekly for three consecutive weeks. The FTFI concentration in maternal serum one day after the 3rd treatment was 260 ng/dL, which was well within the normal range for 32 weeks gestational women. The treatment of thyroxine was continued weekly until delivery. The infant was delivered at 37 weeks of gestation with normal labor, small goiter, normal cord blood TSH and free $T_4$.

Case #2

A pregnant woman, who had a hypothyroid baby discovered at birth in her last pregnancy, had three consecutive maternal serum samples at gestational ages of 20 weeks, 30 weeks and 33 weeks drawn and analyzed for FTFI concentration. All samples had FTFI levels below 1 SD of normal (30 ng/dL, 49 ng/dL, 56 ng/dL).

A diagnosis of potential fetal hypothyroidism was made. The patient began receiving weekly intraaminiotic thyroxine injections (200 µg levothyroxine sodium) on Apr. 29, 1994. The FTFI concentration in maternal serum 6 days following the 3rd treatment was 103 µg/dL (still below 1 SD). However, the urinary FTFI was within normal range [3636 ng/gm creatinine; normal, 2266–6380 ng/gm creatinine)]. The infant was delivered at 38 weeks of gestation; cord blood TSH and free $T_4$ were within normal limits. This case illustrates the usefulness of urinary FTFI in patients who may have a rapid clearance of FTFI from maternal circulation.

Case #3

A pregnant woman had been treated with propylthiouracil (PTU) for Graves' disease in daily doses of 300–500 mg. The PTU dose was reduced to 250 mg/day at the 32nd week of gestation. Ultrasound examination demonstrated fetal goiter. The maternal serum showed a normal $FT_4$ of 0.81 ng/dL (normal 0.5–1.6 ng/dL) and low FTFI [67 ng/dL, (normal 95–195 ng/dL $T_2$S-equivalent)] at 33 weeks of gestation. A diagnosis of potential fetal hypothyroidism was made.

The pregnant woman started to receive weekly thyroxine (levothyroxine sodium, USP, 250 µg) therapy intraamniotically. The ensuing serum FTFI tests were persistently low (69, 70, and 75 ng/dL) between 33 and 35 weeks of gestation despite thyroxine therapy. The infant was delivered at 36 weeks of gestation with elevated TSH (80 µU/mL) and decreased $FT_4$ (0.6 ng/dL) in cord blood.

EXAMPLE #2, PROTOCOL FOR THE DETECTION OF HYPOTHYROID FETUSES AND INTRAUTERINE TREATMENT THEREOF

In order to detect fetal hypothyroidism, fluid samples are obtained from pregnant women according to one of the following protocols: a) monthly serum (2 mL) and urine (10 mL) samples at the beginning of the 2nd trimester (week 14 of gestation); b) one or two consecutive serum and urine samples after 20 weeks of pregnancy; c) one or two consecutive serum and urine samples after 30 weeks of pregnancy.

From these samples, the serum and urine FTFI concentrations and urinary creatinine concentrations are measured.

If serum FTFI concentrations (ng/dL) and/or urinary FTFI concentrations (ng/gm creatinine) are below one standard deviation (SD), other ancillary tests are performed. These tests can include fetal serum thyroid hormone concentrations by cordocentesis, ultrasound to detect the presence of fetal goiter or retesting FTFI concentrations in maternal serum and/or urine samples.

Once fetal hypothyroidism is confirmed using maternal serum FTFI concentrations or maternal urine concentrations in conjunction with the other tests, treatment with intraamniotic administration of higher doses of thyroxine (500 µg/wk) should be started after obtaining the patient's consent. In one case (case #3), the dose of 250 µg/wk may be inadequate to correct fetal hypothyroidism. FTFI concentrations should be determined in maternal serum samples one to three weeks following the initiation of $T_4$ therapy. The treatment should be continued until the baby is delivered.

The present invention can be embodied in other specific forms without departing from its spirit or essential characteristics. The described embodiments are to be considered in all respects only as illustrative and not restrictive. The scope of the invention was, therefore, indicated by the appended claims rather than the foregoing description. All changes which come within the meaning and range of equivalency of the claims are to be embraced within their scope.

I claim:

1. An assay for quantifying fetal thyroid function of a fetus in a pregnant woman, comprising the steps of:

(a) obtaining a sample of fluid from said pregnant woman, wherein said fetus has a gestational age;

(b) determining the amount of Fetal Thyroid Hormone Indicator (FTFI) present in the fluid, said FTFI having the following characteristics: immunological cross-reactivity with $L-T_2$ sulfate ($T_2S$), presence in cord blood at birth, crosses the placenta, presence in maternal blood in an increasing concentration with gestational age in a normal pregnancy, and has a different chromatographic peak than synthetic $T_2S$ in high pressure liquid chromatography; and is also present in maternal urine; and (c) comparing the amount of determined FTFI to a known normal amount of FTFI for the gestational age, wherein a determined amount lower than about 1 standard deviation (SD) of the normal FTFI amount for the gestation age indicates abnormally low thyroid function in said fetus.

2. The method of claim 1, wherein the fluid is maternal blood.

3. The method of claim 1, wherein the fluid is maternal urine.

4. The method of claim 1, wherein the determining step comprises an immunoassay for said FTFI.

5. The method of claim 4, wherein said immunoassay uses an anti-$T_2S$ antibody.

* * * * *